United States Patent [19]
Roth et al.

[11] Patent Number: 6,090,378
[45] Date of Patent: Jul. 18, 2000

[54] COMPOSITION COMPRISING INTERLEUKIN-2 AND THYMIDINE KINASE FOR THE TREATMENT OF TUMORS

[75] Inventors: Claude Roth; Philippe Kourilsky, both of Paris; Lluis Mir, Verrieres-le-Buisson; David Klatzmann; Jean-Loup Salzmann, both of Paris, all of France

[73] Assignees: Institut Pasteur; Institut National de la Sante et de la Recherche Medicale; Universite Pierre et Marie Curie; Assistance Publique-Hopitaux de Paris, all of Paris, France

[21] Appl. No.: 08/895,588

[22] Filed: Jul. 16, 1997

Related U.S. Application Data

[63] Continuation of application No. 08/448,329, filed as application No. PCT/FR94/00192, Feb. 21, 1994, abandoned.

[30] Foreign Application Priority Data

Feb. 22, 1993 [FR] France .................................. 93 02012

[51] Int. Cl.⁷ .................................................... A61K 48/00
[52] U.S. Cl. ........................ 424/93.2; 424/93.21; 514/44
[58] Field of Search ........................... 424/93.21; 514/44; 435/325, 320.1

[56] References Cited

U.S. PATENT DOCUMENTS 5,529,774  6/1996  Barba et al. ........................ 424/93.21

FOREIGN PATENT DOCUMENTS

92/05262  4/1992  WIPO .
9205262   4/1992  WIPO .

OTHER PUBLICATIONS

Hodgson, Exp. Opin. Ther. Pat., 1992 5(5), 459–468.
Culver et al., TIG, 10(5), 1994, 174–178.
Miller et al., FASEB Journal, 9, 1995, 190–199.
Marshall, Science, 269, 1995, 1050–1055.
Plaskin et al., Int. J. Cancer, 52, 1992, 771–777.
Marshall et al. (1995) Science, 269, 1050–1055.
Culver et al. (1994) TIG, 10 (5), 174–178.
Hodgson et al. (1995) Exp. Opin. Ther. Pat., 5 (5), 459–468.
Miller et al. (1995) FASEB, 9, 190–199.

*Primary Examiner*—Deborah Crouch
*Assistant Examiner*—Anne Marie S. Beckerleg
*Attorney, Agent, or Firm*—Oblon, Spivak, McClelland, Maier & Neustadt, P.C.

[57] ABSTRACT

Composition for use in the treatment of tumors and the immunization of humans or animals comprising a synergistic association of cells, viruses, or bacteria expressing, transitorily, in organisms at least one gene for producing in vivo one or more immunomodulators, and viruses, or cells producing viruses, said viruses preferably infecting dividing cells of the treated organisms and carrying within their genome at least one gene whose expression in the dividing cells will cause their destruction.

9 Claims, 1 Drawing Sheet

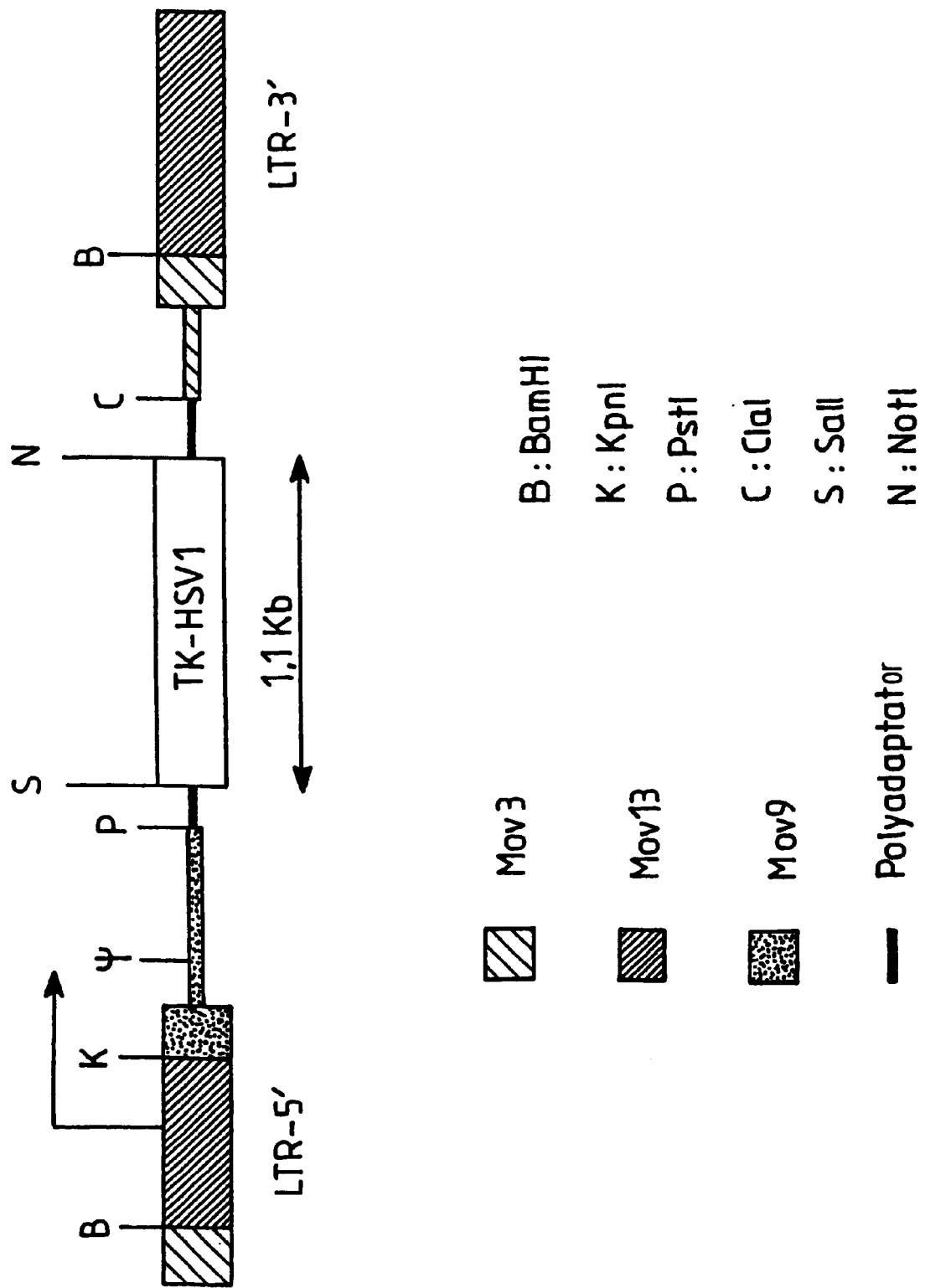

COMPOSITION COMPRISING INTERLEUKIN-2 AND THYMIDINE KINASE FOR THE TREATMENT OF TUMORS

This application is a Continuation of application Ser. No. 08/448,329, filed on Sep. 7, 1995, now abandoned, which was filed as International Application No. PCT/FR94/00192 filed on Feb. 21, 1994.

BACKGROUND OF THE INVENTION

1. Field of the Invention

The present invention relates to a composition for use in the treatment of tumors and the immunization of organisms against tumors.

2. Description of the Related Art

It has been established very recently by various scientific teams that the localized injection, into organisms with a tumour, of synergistic tumour cells producing an interleukin could result in the rejection of this tumour by the organism.

This was demonstrated for Interleukin-2 by Bubenik et al. (Immunology Letters 19, 279–282, 1988; Immunology Letters, 23, 287–292, 1989) and confirmed in particular by Fearon et al. (Cell., 60, 397–403, 1990) and by Ley et al., (European Journal of Immunology 1991, 21: 851–854; Res. Immunol., 1990, 141: 855–863).

The authors of these articles mention that rejection is accompanied by memorization of the response. The animal is therefore vaccinated against subsequent development of the same type of tumour even if the latter is grafted onto a different site.

Synergistic cancer cells producing Interleukin-4 have also been tested with similar results, as reported by Golumbek (Science, 254,713–716,1991) and Tepper et al. (Cell, 57, 503–512, 1989) and also cells producing the tumour necrosis factor (TNF) as described by Blankenstein et al. (J.Exp.Med., 173,1047–1052, 1991).

The possibility has also been put forward (Pardoll, Current Opinion in oncology, Vol.4, N°6, 1124–1129, 1992) of co-introducing into tumour cells derived from the organism to be treated both cytokine encoding genes and suicide genes such as the thymidine-kinase gene of the herpes virus (HSVTK).

The author mentions that this strategy is particularly complicated and requires 100% cell transduction.

This strategy was nevertheless tested in Application N° 92/05262 PCT/US 91/06 612 made by THE JOHN HOPKINS UNIVERSITY and THE UNIVERSITY OF TEXAS SYSTEM which related to compositions intended to potentialize the immune response to a tumour, comprising cells derived from this tumour:

which express an immunopotentializing polypeptide, and have a gene likely to destroy these cells, or a suicide gene.

The immunopotentializing polypeptide may be a cytokine such as interleukin 1 or 2. The suicide gene may, for example, be the thymidine-kinase gene.

The cell compositions that are the subject of this Application are derived from the organism to be treated and are therefore synergistic for this organism. They do not comprise a virus.

The systems described in these publications contain disadvantages for their application in man.

In all these publications the cells producing interleukin are cells from the individual or from a synergistic individual, which are modified to express interleukin.

For the treatment of humans, one disadvantage of this method is the risk that the cells expressing interleukin injected into the organism might continue to develop even after rejection of the tumour.

To remedy this drawback a method of treatment was tested which consists of injecting into the organisms allogeneic or xenogeneic cells expressing genes enabling them to produce in vivo one or more biologically active substances, such as Interleukin-2 (cf. patent application FR 91 14 119 dated Nov. 15, 1991 entitled: "Cell composition for the treatment of human or animal organisms").

This method permits the transient treatment of the organism with these substances as the cells, on account of their immunological nature, are rejected by the organism.

This treatment was tested by injection in the vicinity of the tumour cells (LPB tumour) of Interleukin-2 producing allogeneic cells 9 days after inoculation with the tumour cells. A beneficial effect was observed in the form of diminished tumour growth over several days.

This is a transient effect and, under the conditions used, does not always cause induction of immunity memorization specific to the inoculated tumour cell. In animals treated in this way subsequent inoculation of the same tumour cell (Lewis tumour) can lead to tumour growth.

Moreover the effect observed, that is to say diminished tumour growth, is not always sufficient to cause elimination in the entire tumourous mass.

It will be noted that, in all the experiments described in the state of the art the absence of tumourous growth is generally measured on a healthy animals, and very rarely on pre-established tumors. GOLUMBEK et al.((1991) Science, 254, 713–716) and PORGADOR et al. ((1992) Cancer Res. 52; 3679–3686), for example, injected a composition in both these cases for the purpose of treating a pre-established tumour, but at the time of treatment the pre-established tumour was neither visible nor macroscopically detectable.

With a different approach TROJAN et al.,((1992) Proc. Natl. Acad. Sci., USA, B9, 4874–4878, (1993) Science, 259, 94–97) modified the immunogenicity of a tumour in the rat (glioma) by transfecting the tumour cells with a vector coding for a complementary DNA antisense to IGF 1 (Insulin-like Growth Factor 1). The authors mention that the injection of these modified cells results in the absence of tumorigenicity and in a remote effect on a pre-established tumour. Nevertheless this approach is restricted to tumour cells secreting IGF as autocrine growth factor and it requires the manipulation of each tumour cell to generate a specific immunity response.

Another proposal based on the infection of tumour cells with a retrovirus carrying the gene encoding the thymidine kinase of herpes was tested on two models. In the first model Culver et al. ((1992) Science, 256, 1550–1552) developed a therapeutic approach in which a rat glioma (brain tumour) is injected with xenogeneic cells producing a retroviral vector into which was inserted the gene coding for the herpes thymidine kinase. After local production of TK$^+$ viral particles, which will infect the rapid growth cells (tumour cells), systemic treatment with Ganciclovir (Merck Index, reference 4262), induces massive regression of the pre-established tumourous mass. However this type of treatment is not fully effective since, in the described experiment, complete macroscopic and microscopic tumourous regression was observed in only eleven animals out of the fourteen treated. Also, a small number of tumour cells ($4 \times 10^4$ cells) are injected and treatment (injection of fibroblast cells producing TK$^+$ viral particles) is carried out at a very early stage (from Day 5 onwards) after inoculation of the tumour cells. The major disadvantage nevertheless remains the non-observance in this model of immunity memory vis-à-vis secondary inoculation of the same tumour cells.

The second model develops a relatively similar approach to that mentioned above. Established macroscopic, hepatic tumours are treated by intratumourous injection of xenogeneic fibroblasts producing viral particles expressing the TK gene of the herpes virus and selectively infecting the tumour cells. After a period of transduction of the TK gene in the tumour cells in vivo, most of the tumourous mass is eliminated by treatment with Ganciclovir (GVC). However, the major disadvantages remain the same, namely the absence of any guarantee regarding the full elimination of tumour cells and memorization.

Both these approaches have recourse to xenogeneic cells capable of expressing viral particles able to transduce the TK gene in the tumour cells. The second approach, compared with that developed by Culver et al., is more effective as it mimics a situation of hepatic metastases of primary colon cancer and it is applied to a well developed tumourous site that is macroscopically visible.

Under another technique described in Application N° 93/02556 PCT/US 92/06 188 (UNIVERSITY OF ROCHESTER) cancer patients are reinjected with their own cancer cells into which a suicide gene was introduced.

The tests described in this latter application show that treatment with this type of transgenic cell composition then with the substance relative to the suicide gene, can bring about the destruction in the organism not only of the cells that are the subject of the application but also of other cancer cells. The destruction of transgenic cells in the organism also brings about the destruction of other non-transgenic cancer cells. The compositions described in this application do not comprise any virus.

Finally, a technique based on the combined use of electric impulses and local injections of allogeneic or xenogeneic cells secreting Interleukin-2 has recently been developed (MIR et al., (1992) Compte-Rendu de L'Académie des Sciences de Paris, série III, 314, 539–544).

According to MIR et al. (Eur.J.Cancer 1991, 27, 68–72), electrochimiotherapy consists of locally injecting bleomycine and applying electric impulses in the vicinity of the tumour.

The combined use of these two methods potentialises the anti-tumourous effect observed in each of the two methods used singly.

However, electrochimiotherapy has the major disadvantage, even in combined use with cells secreting Interleukin-2, of being easily applied only in tumours with at least one accessible site.

It therefore arises clearly from the state of the art analysed above that the methods described are not always effective, particularly against established tumours, and that they do not systematically provide immunity memory specific to that tumour or only permit the local treatment of tumours.

SUMMARY OF THE INVENTION

The applicants therefore sought to find a composition with which to obtain firstly the fast disappearance of the tumour wherever it may be localised, and secondly the long-term, specific immunization of the organism against the treated tumour.

They subsequently found, in surprising manner, that with the combination of immunomodulator secretion means and vectors leading specifically to the suicide of tumour cells, it is most often possible to obtain the rapid, definitive disappearance of the tumour and specific long-term immunization of the organism against this tumour.

The subject of the present invention therefore is a composition for use in the treatment of tumours in human or animal organisms and to immunize them against this tumour, said composition comprising a synergistic association of:

cells, viruses or bacteria transiently expressing in the organism at least one gene enabling them to produce in vivo one or more immunomodulators, and viruses, or cells producing viruses, said viruses if possible preferably infecting dividing cells of the treated organisms and carrying within their genome at least one gene whose expression in the dividing cells will cause their destruction.

BRIEF DESCRIPTION OF THE DRAWING

FIG. 1 is a schematic of the pMTK vector.

DETAILED DESCRIPTION

Advantageously, the composition such as described above is comprised of cells producing in vivo one or more immunomodulators and in addition producing viruses carrying within their genome at least one gene whose expression in the dividing cells will cause their destruction.

The cells used in these compositions shall preferably be allogeneic or xenogeneic cells so that they may be eliminated from the treated organisms. They may themselves be infected by or be producers of viruses carrying within their genome at least one gene whose expression in the dividing cells will cause their destruction such as defined above.

Said composition may thus comprise cells in which the virus used to infect the dividing cells of the organism is responsible for the production of the immunomodulator.

The immunomodulators are advantageously Interleukin-2, Interleukin-4, Interleukin-7, the Tumour Necrosis Factor (TNF), Interferon-gammma, GM-CSF (Granulocyte-Macrophage Colony Stimulating Factor), alone or in combination.

These immunomodulators may, in addition to the cells and bacteria mentioned above, be expressed from genes carried on the virus genome, such as retroviruses, Pox viruses (vaccine virus, Canary Pox), Adenoviruses and defective Adenovirus associated viruses (AAV).

The bacteria may be intracellular bacteria producing an immunomodulator.

It will be noted that the immunomodulators may be brought by any means, in addition to cells, bacteria or viruses, enabling the release of immunomodulators in the organism; one such means for example is a grafted micropump releasing immunomodulators in the organism.

The viruses preferably infecting the dividing cells of the treated organism and carrying within their genome at least one gene whose expression in the dividing cells will cause their destruction, or lysis agents, are preferably retroviruses, Pox viruses or Adenoviruses. These viruses will be all the more advantageous if they have the property of infecting or destroying preferably and for the most part the dividing cells of the organism.

They may be brought by selected cells so that they may be eliminated rapidly in the organisms, particularly allo- or xenogeneic cells.

The gene whose expression in the dividing cells will cause their destruction is preferably the gene of a thymidine kinase or a cytostine deaminase. The destruction of the cells carrying these genes shall be induced by supplying then respectively with Ganciclovir and 5-fluorocytidine.

The present invention also relates to the use of the above described composition for the manufacture of a medicinal product for the treatment of tumours and cancers and for the immunization of the organisms against these illnesses.

Advantageously all the elements of the composition are administered simultaneously. They may be given simultaneously or independently.

It is also possible to administer the two main components with a time delay. Advantageously, therefore, the viruses or the cells producing viruses are administered firstly, preferably infecting the dividing cells of the organism and carrying within their genome at least one gene whose expression in the dividing cells will cause their destruction, followed by the substrates whose metabolisation by the dividing cells will cause their destruction.

This elimination phase of the tumourous mass is followed by an immunization phase of the organism against this tumour by administration of cells, viruses or bacteria expressing the immunomodulators.

The composition according to the invention may be introduced by any means available to men of the art, particularly by syringe injection under medical imaging.

Advantageously this treatment is local but it may equally well be systemic.

The present invention is illustrated by the example below with reference to the appended single figure which represents the retroviral pMTK vector map.

EXAMPLE

Treatment of Mice with Tumours Using Cells Secreting Interleukin-2 and Producing the PMTK Retrovirus.

C56 BL/6 mice with tumours were treated with a composition containing allogeneic cells producing Interleukin-2 and the PMTK retrovirus which carries the thymidine kinase gene of the HSV1 virus.

Injections were made in the vicinity of the tumours.

The pMTK vector (see figure) has the following characteristics:

LTR-5'

Mov3 as far as the BamHl site (−350 from the start of the transcription),

Mov13 of the BamHl site (−350) as far as the Kpnl site (+30)

Mov9 of the Kpnl site (+30) as far as the Pstl site (+560) (contains the packaging sequence)

The non-coding sequence at 3' of the Clal site (+7674) as far as U3 (+7817) is derived from Mov3.

LTR-3'

Mov3 as far as the BamHl site positioned at 7910 (or−350),

Mov13 as far as the end of U5.

A CRIP packaging cell line is co-transfected with the pMTK plasmid (20 μg) and the pWLNeO plasmid (1 μg). Several clones were isolated at G418 selection.

The strength of the selected clone was $5.10^5$ infectious particles/ml as measured by the ability to confer HAT resistance (Hypoxanthine, Aminopterine, Thymidine) for L $TK^+$ cells. The infection of L $TK^-$ cells is performed with successive dilutions of the supernatant containing viral particles.

What is claimed is:

1. A composition comprising:

cells which are allogeneic or xenogeneic for mammal, wherein said cells comprise a gene encoding Interleukin-2, and a retrovirus which infects dividing cells of mammal, wherein said retrovirus comprises a gene encoding thymidine kinase.

2. The composition of claim 1, wherein the retrovirus is produced by the cells expressing Interleukin-2.

3. A method for treating tumours comprising:

a) administering at or adjacent to a tumor in a mammal in need of such treatment a tumor-reducing amount of the composition of claim 1, and b) administering to the mammal a substrate which is metabolized by the cells of the tumor; wherein the production of thymidine kinase in the presence of the metabolized substrate results in an inhibition of tumor growth.

4. The method of claim 3, wherein said cells comprising a gene encoding Interleukin-2 and the retrovirus comprising the thymidine kinase gene are administered simultaneously.

5. The method of claim 3, wherein said cells comprising a gene encoding Interleukin-2 and the retrovirus comprising the thymidine kinase gene are administered independently.

6. A method for treating tumors comprising:

a) administering at or adjacent to a tumor in a mammal in need of such treatment a tumor-reducing amount of the composition of claim 3, and b) administering to the mammal a substrate which is metabolized by the cells of the tumor; wherein the production of thymidine kinase in the presence of the metabolized substrate results in an inhibition of tumor growth.

7. The method of claim 3, wherein the cells producing the Interleukin-2 are replaced by a means for locally administering Interleukin-2 in the mammals.

8. The method of claim 7, wherein the means for locally administering Interleukin-2 is a micropump.

9. The method of claim 3, wherein said retrovirus is produced by retrovirus producer cells which are allogeneic or xenogeneic for a mammal, and wherein said retrovirus producer cells are administered prior to or simultaneously with the administration of said allogeneic or xenogeneic cells which encode a gene for interleukin-2.

* * * * *